(12) United States Patent
Oikawa et al.

(10) Patent No.: US 6,243,440 B1
(45) Date of Patent: Jun. 5, 2001

(54) RADIOGRAPHIC APPARATUS

(75) Inventors: Shiro Oikawa; Susumu Adachi; Takayuki Takemoto, all of Kyoto; Yasukuni Yamane, Osaka, all of (JP)

(73) Assignees: Shimadzu Corporation, Kyoto; Sharp Kabushiki Kaisha, Osaka, both of (JP)

( * ) Notice: Subject to any disclaimer, the term of this patent is extended or adjusted under 35 U.S.C. 154(b) by 0 days.

(21) Appl. No.: 09/299,075

(22) Filed: Apr. 26, 1999

(30) Foreign Application Priority Data

Apr. 28, 1998 (JP) .................................................. 10-118801

(51) Int. Cl.[7] ........................................................ H05G 1/64
(52) U.S. Cl. ............................................ 378/98.8; 378/98.7
(58) Field of Search ..................................... 378/97, 96, 95, 378/98.2, 98.7, 98.8, 106, 108

(56) References Cited

U.S. PATENT DOCUMENTS 4,803,714 * 2/1989 Vlasbloem et al. .................... 378/62
5,262,649  11/1993 Antonuk et al. .
5,608,775 * 3/1997 Hassler et al. ...................... 378/98.8

FOREIGN PATENT DOCUMENTS

| 0063644 | * 11/1982 | (EP) | ..................................... 378/108 |
| 59-211263 | 11/1984 | (JP) . | |
| 2-164067 | 6/1990 | (JP) . | |
| 7-72259 | 3/1995 | (JP) . | |

* cited by examiner

Primary Examiner—David P. Porta
(74) Attorney, Agent, or Firm—Arent, Fox, Kintner, Plotkin, Kahn PLLC (57) ABSTRACT

An apparatus using a two-dimensional radiation sensor for acquiring X-ray penetration images or the like. A monitoring radiography is performed with a small dose before a production radiography. A radiographic condition for the production radiography, specifically a radiation emitting period or a tube current of a radiation generator, is computed based on a ratio between a quantity of charges in a region of interest collected from the two-dimensional radiation sensor in time of the monitoring radiography and a desired quantity of charges in the region of interest in time of the production radiography. The production radiography is carried out based on a result of the computation to acquire a high quality image.

12 Claims, 6 Drawing Sheets

RADIOGRAPHIC APPARATUS

BACKGROUND OF THE INVENTION

(1) Field of the Invention

This invention relates to a radiographic apparatus for use in medical radiography or industrial nondestructive inspection, for example.

(2) Description of the Related Art

Conventionally, plain radiographic apparatus employing X-ray film and imaging plates have been used in mass medical examinations for tuberculosis and lung cancer. In recent years, apparatus have been developed which enable real-time reading by means of two-dimensional X-ray sensors (hereinafter referred to as flat panel sensors) (e.g. Japanese Patent Publication (Unexamined) S59-211263 and Japanese Patent Publication (Unexamined) H2-164067).

Flat panel sensors include the direct conversion type and indirect conversion type. A flat panel sensor of the direct conversion type has a plurality of switching elements (TFT switches) arranged in a matrix form on a flat panel, with a semiconductor layer superposed thereon. X-ray photons are converted into electric signals in the semiconductor layer to output a fluoroscopic image in electric digital signals. A flat panel sensor of the indirect conversion type has photodiodes and switching elements connected together and arranged in a matrix form, with a layer of scintillator (fluorescent substance) superposed on this photodiode array (semiconductor layer). X rays incident on the scintillator generate optical signals which are converted into electric signals in the photodiodes.

In these flat panel sensors, gate lines common to the respective columns are connected to the switching elements of pixels. A drive signal transmitted to the gate lines turns on the switching elements in the respective columns, whereby charge signals of the pixels are outputted from data lines common to the respective rows. The charge signals outputted are inputted to a signal reading circuit. After a charge-to-voltage transduction and amplification, the signals are put to an analog-to-digital conversion pixel by pixel, and then inputted to an image processing device or the like.

Conventionally, the plain radiographic apparatus employs a separate phototimer in order to avoid underexposure and overexposure. The phototimer has a semiconductor X-ray sensor disposed opposite a front surface of X-ray film (X-ray incidence surface). At an actual radiographing time, the phototimer monitors X-ray doses incident on the X-ray sensor, and a time for terminating the radiography is determined by checking whether an integrated value thereof has exceeded a predetermined value or not.

Such a method, however, poses a problem that the shadow of the phototimer falls on X-ray film. Where the phototimer is formed so thin as not to appear on radiographic images, a required level of X-ray sensitivity cannot be secured.

A proposal has been made recently to achieve an optimal radiography of the same purport with the flat panel sensor developed (e.g. Japanese Patent Publication (Unexamined) H7-72259). The gist of the invention described in this publication lies in frequently taking and adding readings from a predetermined monitor pixel during X-ray irradiation, and blocking X rays when the sum reaches a predetermined quantity.

However, the invention described in Patent Publication H7-72259 has a disadvantage that a reading operation eliminates all data relating to a column that shares a gate line with the monitor pixel. It is conceivable to store the data in a memory to use the data afterward as a radiograph. However, in an actual situation, there occurs a time drift or a lag in reading time, which results in a difference in image quality between the column including the monitor pixel from which data are read frequently, and the other columns of ordinary pixels.

SUMMARY OF THE INVENTION

This invention has been made having regard to the state of the art noted above, and its object is to provide a radiographic apparatus for acquiring radiographic images with a two-dimensional X-ray sensor, which is capable of performing radiography with optimal exposure and acquiring images of uniform quality at all times.

The above object is fulfilled, according to this invention, by a radiographic apparatus using a two-dimensional radiation sensor, comprising:

a radiation generator for irradiating an examinee;

the two-dimensional radiation sensor having detecting elements in a two-dimensional array for converting radiation transmitted through the examinee into charge signals, and switches connected to the detecting elements, respectively;

a gate driving circuit for successively driving, column by column, the switches connected to the detecting elements of the two-dimensional radiation sensor;

a signal reading circuit for transducing to voltages, amplifying and digitizing electric charges outputted from data lines of the two-dimensional radiation sensor;

a control circuit for controlling the gate driving circuit and the signal reading circuit;

a sequence controller for controlling a radiation generating sequence of the radiation generator to perform a monitoring radiography and a subsequent, production radiography with respective radiographic conditions; and a radiographic condition computing unit for computing a radiographic condition for the production radiography based on a ratio between a quantity of charges collected from the two-dimensional radiation sensor through the signal reading circuit in time of the monitoring radiography and a desired quantity of charges in time of the production radiography, and applying the radiographic condition for the production radiography at least to the sequence controller.

The radiographic apparatus according to this invention determines a radiographic condition for production radiography based on a ratio between a quantity of charges collected from the two-dimensional radiation sensor in time of monitoring radiography and a desired quantity of charges in time of the production radiography. Thus, the production radiography is carried out constantly under an optimal radiographic condition. Moreover, in this invention, information (i.e. the charges collected) for determining a radiographic condition is collected through the monitoring radiography preceding the production photography. The invention does not execute a process in time of production radiography to acquire information from a particular detecting element to determine a radiographic condition. Thus, there occurs no lowering of a signal level with a column including the particular detecting element, thereby assuring an image of uniform quality.

The radiographic condition computing unit may compute an irradiating period or a tube current of the radiation generator as the radiographic condition for the production radiography.

Though not limitative, the following techniques may be adopted for determining the radiographic condition for the production radiography:

(1) Regarding, as the quantity of charges collected, an integrated value of charges of those of the detecting elements present in a region of interest among the charges of the detecting elements of the two-dimensional radiation sensor acquired through the monitoring radiography, and computing the irradiating period based on a ratio between the quantity of charges collected and an integrated value of a desired quantity of charges in the region of interest in time of the production radiography; and (2) Regarding, as the quantity of charges collected, a charge of one of the detecting elements having a maximum value in a region of interest among the charges of the detecting elements of the two-dimensional radiation sensor acquired through the monitoring radiography, regarding, as the desired quantity of charges, a maximum charge within a range where the two-dimensional radiation sensor has linear input/output characteristics, and computing the irradiating period based on a ratio between the quantity of charges collected and the desired quantity of charges, With the latter technique (2) in particular, all the pixels in the region of interest obtained through the production radiography are those present within the range where the two-dimensional radiation sensor has linear input/output characteristics. None of these pixels are charge-saturated, to realize a high quality image.

The radiation generating sequence is not limitative. For example, X rays may be emitted for the monitoring radiography, then stopped, and thereafter emitted for the production radiography. In this case, the charges are read from the two-dimensional radiation sensor during an X-ray non-emission period following the monitoring radiography and preceding the production radiography, to determine a radiographic condition for the production radiography.

In a different radiation generating sequence, X rays are emitted continuously for the monitoring radiography and the production radiography. In this case, the charges are read from the two-dimensional radiation sensor while X rays are emitted for the monitoring radiography. Such reading of the charges provides an advantage of reducing a time required for radiography. However, while the charges are read from a particular column in the two-dimensional radiation sensor, the other columns are irradiated with X rays, resulting in variations in the X-ray irradiating period occurring from column to column. Such variations in the X-ray irradiating period bring about gradual density variations in an image produced. It is therefore preferable to adjust, column by column, the charges read from the two-dimensional radiation sensor according to variations in the X-ray irradiating period.

Preferably, when the desired quantity of charges exceeds a maximum quantity within a range where the two-dimensional radiation sensor has linear input/output characteristics, the radiation generating sequence is controlled to carry out the production radiography a plurality of times, whereby the charges of the detecting elements of the two-dimensional radiation sensor acquired through the production radiography carried out once fall within the range where the two-dimensional radiation sensor has linear input/output characteristics. Images acquired from the production radiography carried out a plurality of times are added to form one image. Consequently, a high quality image is obtained as where a two-dimensional radiation sensor with a large dynamic range is used.

BRIEF DESCRIPTION OF THE DRAWINGS

For the purpose of illustrating the invention, there are shown in the drawings several forms which are presently preferred, it being understood, however, that the invention is not limited to the precise arrangement and instrumentalities shown.

DESCRIPTION OF THE PREFERRED EMBODIMENTS

Preferred embodiments of the present invention will be described in detail hereinafter with reference to the drawings.

Figure 1:
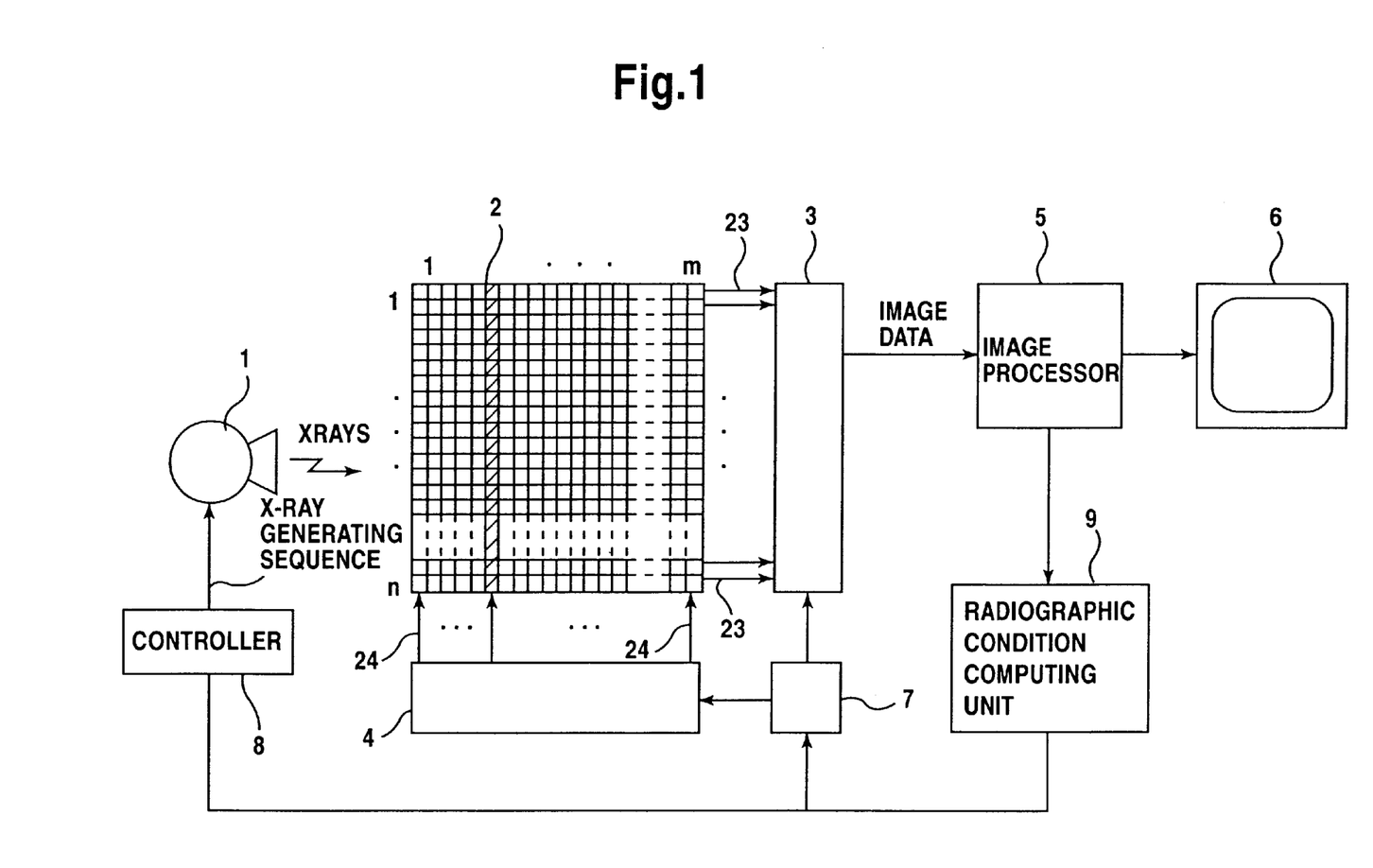
FIG. 1 is a block diagram showing an embodiment of this invention.

FIG. 1 is a block diagram showing an embodiment of this invention.

Figure 2:
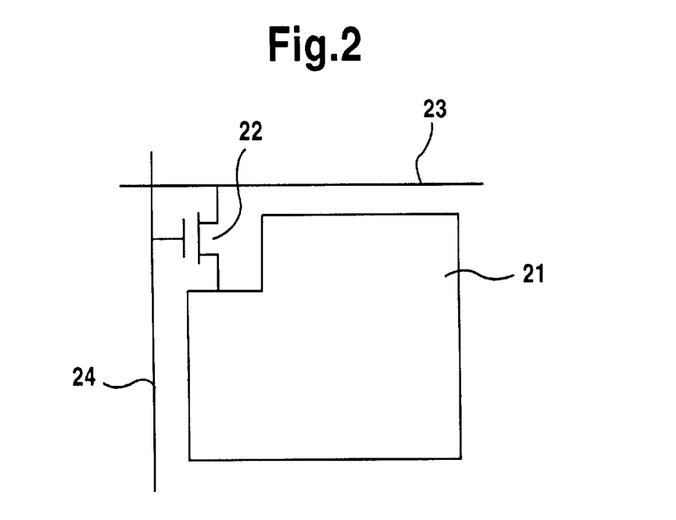
FIG. 2 is a view schematically showing a construction, corresponding to one pixel, of a two-dimensional X-ray sensor used in the embodiment.

X rays emitted from an X-ray generator 1 penetrate an examinee (not shown) and irradiate pixels of a two-dimensional X-ray sensor 2. The two-dimensional X-ray sensor 2 has m×n pixels, and a scintillator (not shown) disposed on an X-ray incidence surface. As shown in FIG. 2, each pixel of two-dimensional X-ray sensor 2 includes a photodiode 21 responsive to light to output an electric charge, and a TFT switch 22 connected thereto.

When X rays enter the two-dimensional X-ray sensor 2, the scintillator disposed on the X-ray incidence surface of the sensor 2 outputs an optical signal proportional to an incident X-ray dose to cause the photodiodes 21 to generate charge signals. The TFT switches 22 have m gate lines 24 common to respective columns. When a drive signal is applied from a gate driving circuit 4 to each gate line 24, the TFT switches 22 in that column are turned on. Then, accumulated charge signals of the pixels in that column are outputted from data lines 23 common to respective rows. These charge signals are inputted to a signal reading circuit 3. The signals, after a charge-to-voltage transduction and amplification, are put to an analog-to-digital conversion pixel by pixel, and inputted as image data to an image processing device 5. The image data of each pixel inputted to the image processing device 5 is stored in a memory (not shown) in the image processing device 5. Subsequently, the data is ultimately displayed as an X-ray image on an image display device 6 such as a TV monitor.

The gate driving circuit 4 and signal reading circuit 3 are controlled by a control circuit 7. The X-ray generator 1 is driven and controlled by a controller (sequence controller) 8.

This embodiment is characterized by an X-ray generating sequence for driving the X-ray generator 1 to perform a monitoring radiography with a small dose in advance and then to performs an actual or production radiography. Image data collected in the monitoring radiography is inputted to a radiographic condition computing unit 9 which carries out computations as set out hereinafter, and transmits an X-ray irradiation stopping signal to the X-ray generator 1 and control circuit 7 (or a tube current setting signal to the X-ray generator 1 in a modified embodiment). The X-ray generating sequence is set to the controller 8 which drives and controls the X-ray generator 1.

Examples of computation performed by the radiographic condition computing unit 9 will be described hereinafter with reference to radiographic sequences shown in FIGS. 3 through 8.

Figure 3:
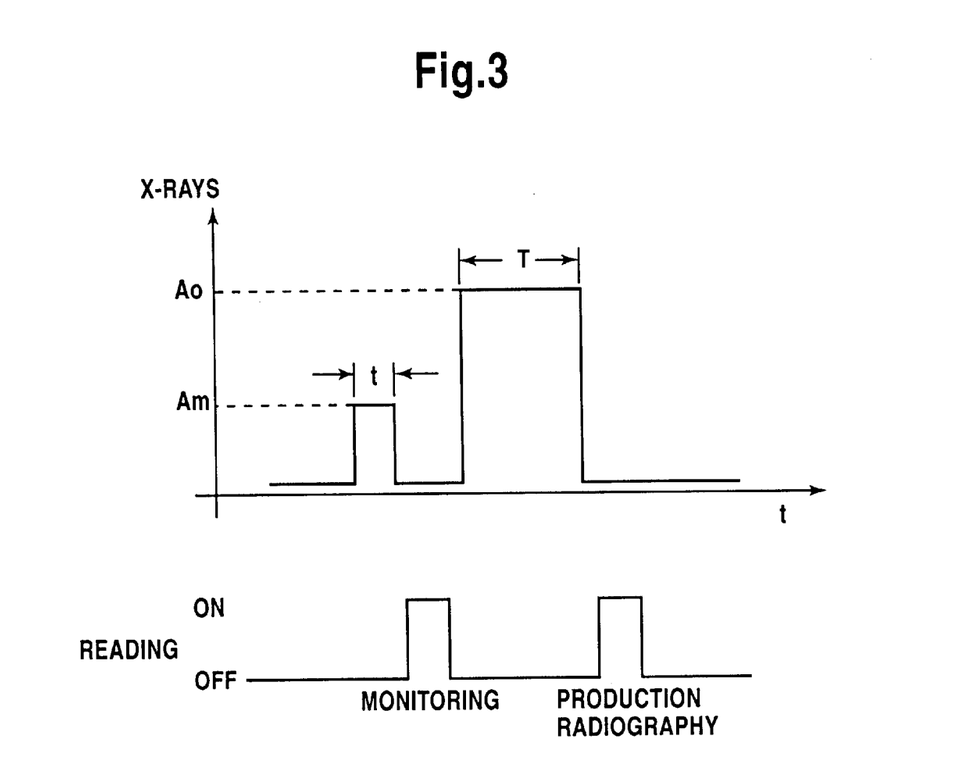
FIG. 3 is a view showing a radiographic sequence executed in the embodiment of this invention.

The time chart in the upper half of FIG. 3 shows an X-ray generating sequence. The vertical axis represents tube current values of the X-ray generator 1. The time chart in the lower half is a reading sequence showing, in a simplified form, gate drive signal trains transmitted for reading purposes from the gate driving circuit 4 to the two-dimensional X-ray sensor 2 shown FIG. 1.

In this radiographic sequence, the flat panel sensor is first reset (charges in the pixels over the entire panel surface are read, i.e. initialized). Then, the first duration t in the X-ray generating sequence is a period for accumulating a monitor image. Subsequently, a gate drive signal train is transmitted in the "monitor" portion of the reading sequence to read the monitor image.

The monitor image acquired in the above sequence may often be in a lower resolution than an image to be acquired through a production radiography. Thus, a plurality of adjacent gate lines may be turned on at the same time, or a plurality of adjacent reading signals may be bound together (in what is known as pixel binding) to reduce the time required for the monitoring radiography. To minimize X-ray irradiation of the examinee, the monitoring radiography, preferably, uses an X-ray dose not exceeding 10 percent of the dose used in the production radiography. This means in the radiographic sequence of FIG. 3;

$$Am \cdot t < A_0 \cdot T \cdot 0.1$$

where T is an X-ray irradiating period for the production radiography, $A_0$ is an X-ray tube current value for the production radiography, and Am is an X-ray tube current value for the monitoring radiography.

Figure 9:
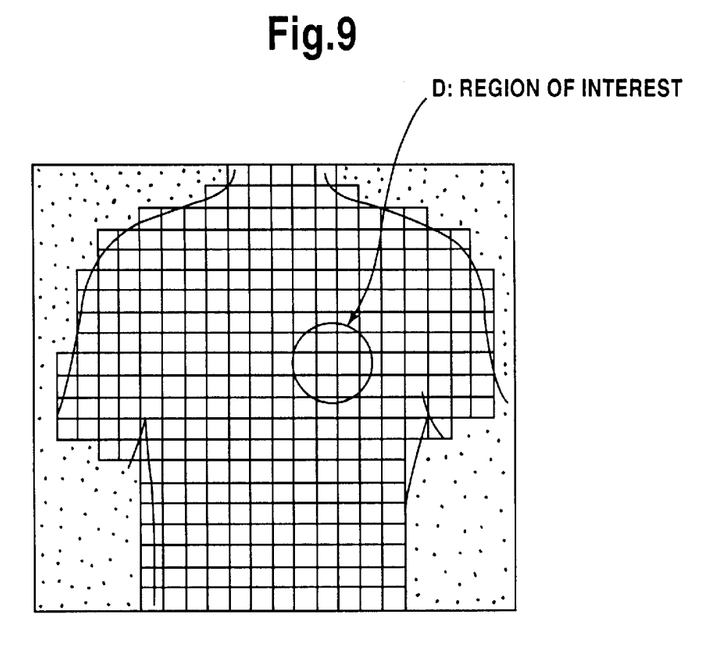
FIG. 9 is a view showing one example of monitor images.

When a monitor image of low resolution is displayed on the image display device 6 in the monitoring radiography, the operator, while looking at the monitor image, sets a region of interest D as shown in FIG. 9. The image display device 6 transmits image data of each pixel in the region of interest D to the radiographic condition computing unit 9. The radiographic condition computing unit 9 adds up the image data in the region of interest D to determine a quantity of monitoring charges Qm. Assuming a desired quantity of charges in the region of interest D for the production radiography to be $Q_0$, and that an X-ray tube current value $A_0$ is set beforehand for the production radiography, an X-ray irradiating period (T) for the production radiography is derived from the following equation:

$$T = (Am/A_0) \cdot (Q_0/Qm) \cdot t \quad (1)$$

Figure 10:
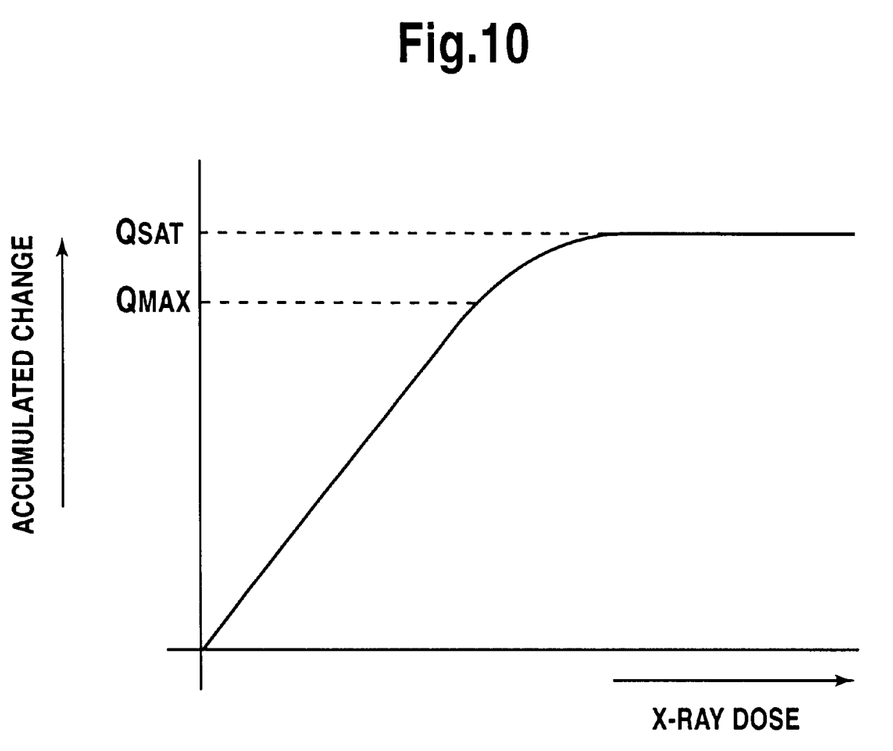
FIG. 10 is a graph showing input/output characteristics of X-ray doses incident on the two-dimensional X-ray sensor (input) and charges accumulated in pixels (output).

The desired quantity of charges $Q_0$ in the region of interest D for the production radiography is determined as follows. Reference will be made to FIG. 10. FIG. 10 is a graph showing input/output characteristics of X-ray doses (integrated value) incident on the two-dimensional X-ray sensor 1 and charges accumulated in the pixels. In the range of relatively small X-ray dose, the X-ray dose and the quantity of accumulated charges have an excellent linear relationship (linearity). As the X-ray dose increases and the quantity of accumulated charges exceeds $Q_{MAX}$, the linear relationship deteriorates gradually and the quantity of accumulated charges becomes saturated. It is inconvenient in acquiring density variations in the image corresponding to X-ray doses that the quantity of accumulated charges becomes saturated during the X-ray irradiating period T in the production radiography. Thus, a quantity of charges smaller than a saturated quantity of accumulated charges $Q_{SAT}$ (preferably the quantity of accumulated charges $Q_{MAX}$) in the region of interest is appropriately set as the desired quantity of charges $Q_0$ in the region of interest. For example, the desired quantity of charges $Q_0$ in the region of interest is set to be 60 to 80% of the saturated quantity of accumulated charges $Q_{SAT}$. Actually, once a desired quantity of charge (desired unit quantity of charge) is designated for one pixel, the radiographic condition computing unit 9 multiplies the desired unit quantity of charge by the number of pixels in the region of interest D, and sets the integrated value thereof as $Q_0$ in the equation (1) above.

For the above computing process, the operator designates the region of interest D while looking at the monitor image on the image display device 6. Where a region of interest is determined beforehand from image information acquired earlier, a production radiography may be carried out by automatically computing an X-ray irradiating period from a monitoring radiography based on the relational equation noted above, without requiring an operation by the operator.

In the above computing process, where resolution is different between the monitoring radiography and production radiography, the equation (1) above may be changed to a relational equation taking this aspect into account. Where, for example, the number of pixels in the region of interest D for the monitoring radiography is ¼ of the number of pixels for the production radiography (i.e. ¼ resolution), the quantity of monitoring charges "Qm" in the equation (1) above may only be replaced with "4Qm".

In the above embodiment, an integrated value of image data in the region of interest D is used as the quantity of monitoring charges Qm in the equation (1), and variations in the quantity of charges of the pixels in the region of interest D are not taken into account. That is, it cannot be said that none of the pixels in the region of interest D are saturated in time of production radiography. The next embodiment relates to a technique of determining an X-ray irradiating period T for saturating none of the pixels in the region of interest D.

Production radiography is performed here in a range of excellent linearity in the input/output characteristics of two-dimensional X-ray sensor 1, that is within the range of the maximum quantity of charges $Q_{MAX}$ (FIG. 10). In this case, the quantities of charge of the pixels in the region of interest D in the monitor image are compared, and a pixel with the largest quantity of charge is automatically selected as a key pixel. The maximum quantity of charges $Q_{MAX}$ is applied as $Q_0$, and the quantity of charge of the key pixel as Qm in the equation (1) above. That is, an X-ray irradiating period T for production radiography is derived from the following equation (2):

$$T = (Am/A_0) \cdot (Q_{MAX}/Qm) \cdot t \quad (2)$$

In this case, the X-ray irradiating period T for production radiography is determined based on the key pixel with the largest quantity of charge in the region of interest D. The other pixels in the region of interest D constantly have quantities of charges smaller than a quantity of accumulated charge of the key pixel. Thus, none of the pixels become saturated. According to this embodiment, no charge-saturated region is formed in the panel in time of production radiography regardless of the thickness of and the level of absorption by the examinee. Radiography is effected within the range of excellent linearity.

In the radiographic sequence shown in FIG. 3 and the computing process therein, the X-ray irradiating period for production radiography is derived from the equation (1) or equation (2). This invention is not limited thereto. The invention includes, within its scope, a case where an X-ray irradiating period (T) is set beforehand as a system set value, and production radiography is started after determining an X-ray tube current value ($A_0$) as a result of computation. This aspect is applicable to the modifications described hereinafter with reference to FIGS. 4 through 8.

In that case, the X-ray tube current value ($A_0$) may be derived from the following equations:

$$A_0 = (t/T) \cdot (Q_0/Qm) \cdot Am \quad (3)$$

$$A_0 = (t/T) \cdot (Q_{MAX}/Qm) \cdot Am \quad (4)$$

The equation (3) corresponds to the embodiment using the equation (1), and is used for determining X-ray tube current value $A_0$ for production radiography based on a ratio between the integrated value Qm of image data in the region of interest D of a monitor image and the desired quantity of charges $Q_0$ (integrated value) in the region of interest D. The equation (4) corresponds to the embodiment using the equation (2), and is used for determining X-ray tube current value $A_0$ for production radiography based on a ratio between the quantity of accumulated charge Qm of the key pixel with the largest quantity of charges in the region of interest D of a monitor image and the maximum quantity of charges $Q_{MAX}$ of the panel with linearity.

Various modifications of the radiographic sequence will be described next.

Figure 4:
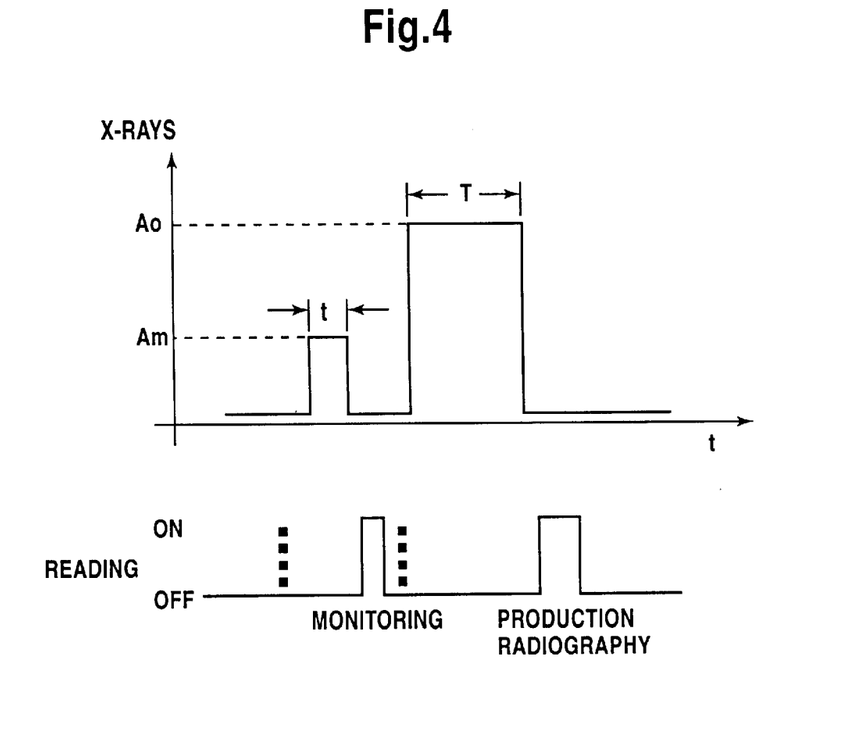
FIG. 4 is a view showing modification 1 of the radiographic sequence.

FIG. 4 shows modification 1 of the radiographic sequence.

In the radiographic sequence shown in FIG. 4, accumulated charges are cleared from the entire panel surface immediately before starting X-ray irradiation for production radiography. This step eliminates a difference in accumulated charge between a portion from which a monitor image is read and the other portions. Such a reset operation (a thick vertical dotted line in the reading sequence) is carried out by transmitting ON signals simultaneously from the gate driving circuit 4 to the two-dimensional X-ray sensor 2 shown in FIG. 1, covering all columns used in the production radiography. The radiographic sequence in FIG. 4 includes also a reset operation preceding an X-ray generating sequence for the monitor image.

Though not described, each of the radiographic sequence shown in FIG. 3 and the modifications described hereinafter with reference to FIGS. 5 through 8 includes a reset operation or a panel initialization similar thereto which is carried out before the X-ray generating sequence for a monitor image.

In FIGS. 3 and 4, the X-ray generating sequence is separated in time for the monitoring radiography and production radiography. In the modifications shown in FIGS. 5 through 8, the first half of a continuous X-ray generating period is allocated to the monitoring radiography. This is applicable to a case where an X-ray irradiating time or X-ray tube current value for production radiography is determined automatically from information obtained from the monitoring radiography (one of the equations (1)–(4) noted hereinbefore).

Figure 5:
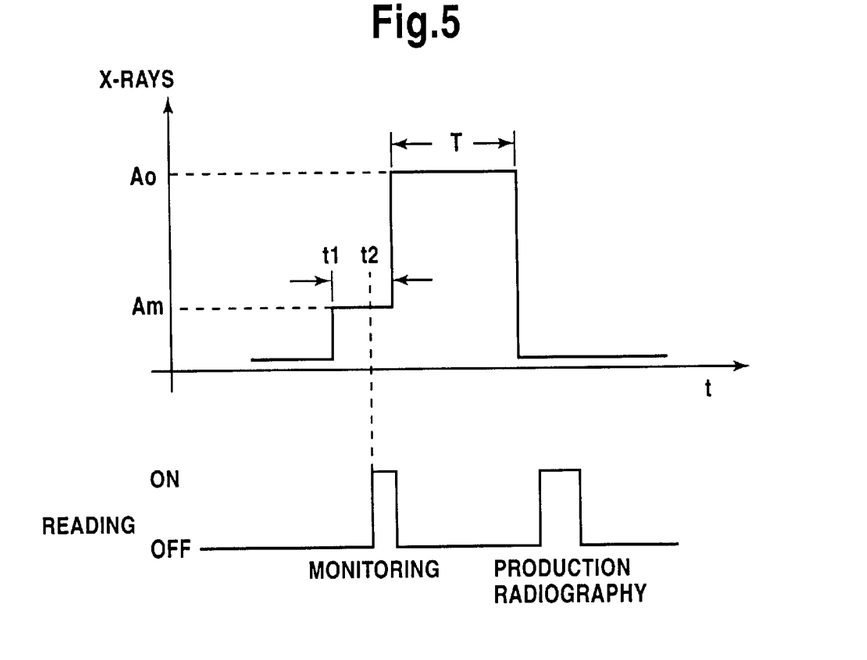
FIG. 5 is a view showing modification 2 of the radiographic sequence.

In the radiographic sequence shown in FIG. 5, the monitoring radiography and reading are carried out in the first range having a small X-ray tube current value. In the radiographic sequence shown in FIG. 6, the monitoring radiography and reading are carried out in the first half of an X-ray generating period having a fixed X-ray tube current value.

The radiographic sequence of FIG. 6 will be described in greater detail.

Figure 6:
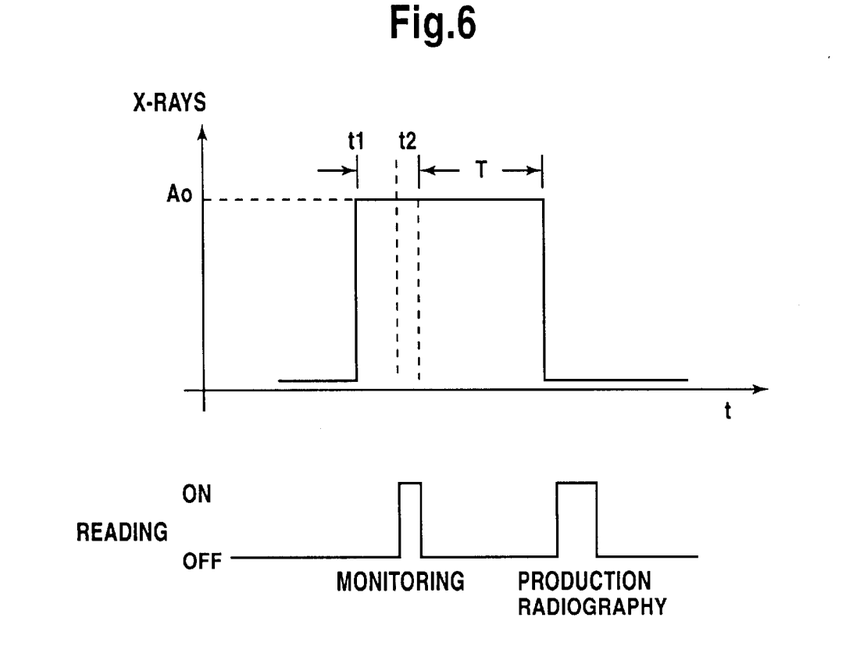
FIG. 6 is a view showing modification 3 of the radiographic sequence.

In the radiographic sequence shown in FIG. 6, upon lapse of a period t1 after starting X-ray irradiation for monitoring radiography, accumulated charges are read sequentially, column by column, from the first column onward. A period t2 is required from reading of accumulated charges from the first column to reading of accumulated charges from the final, mth column. Since the X-ray irradiation is continued during the reading period, each pixel in the mth column receives X rays until the accumulated charge is read, for a time longer by the period t2 than each pixel in the first column. That is, the monitor image has a difference in the intensity of accumulated charge from column to column (in a gentle density gradient from the first column to the mth column). To eliminate the difference, the following process is executed in this example.

In the two-dimensional X-ray sensor 2 shown in FIG. 1, the X-ray irradiating period is t1 for the pixels in the first column, and t1+t2 for the pixels in the mth column. The monitor image is formed by reducing this difference in the irradiating period. Specifically, the accumulated charges read from each column are multiplied by a weighting coefficient corresponding to the difference in X-ray irradiating time from the first column to the mth column. In this way, the accumulated charges are adjusted for each column to form the monitor image, with the results corresponding to the case of all the columns being irradiated with X rays for the same period of time. The monitor image is used to determine the quantity of monitor charges (Qm) in the region of interest D, and an X-ray irradiating period (T) for production radiography is derived from the equation (2), for example.

In the image resulting from the production radiography also, the X-ray irradiating period is t2+T for the pixels in the first column, and T for the pixels in the mth column. Preferably, the image is formed by reducing the difference (i.e. standardizing image intensity). In order to avoid such a problem occurring with the radiographic image, a reset operation may be carried out after the monitor image is read, thereby to equalize the X-ray irradiating period (T) for production radiography for all pixels.

Next, a plurality of reading steps will be described, which are executed in modification 4 shown in FIG. 7 and modification 5 shown in FIG. 8.

In these modifications, a plurality of reading steps (in production radiography) are executed to compensate for a narrow dynamic range of the X-ray sensor. By adding the images acquired, the dynamic range of the X-ray sensor is enlarged in an equivalent manner. Specifically, in the examples shown in FIGS. 7 and 8, when a desired quantity of charges $Q_0$ is larger than $Q_{MAX}$, an X-ray irradiating time T that does not produce a charge-saturated region in the panel in time of production radiography is derived from the equation (2) based on information acquired through collection of the monitor image. The production radiography for the X-ray irradiating time T is performed a plurality of times. The number of times is determined in the example of FIG. 7 from equation (5), and in the example of FIG. 8 from equation (6).

$$N=[Q_0/Q_{MAX}]+2 \quad (5)$$

$$N=[Q_0/Q_{MAX}]+1 \quad (6)$$

In the above equations, $[Q_0/Q_{MAX}]$ means an integral part of a calculated value of $Q_0/Q_{MAX}$.

Figure 7:
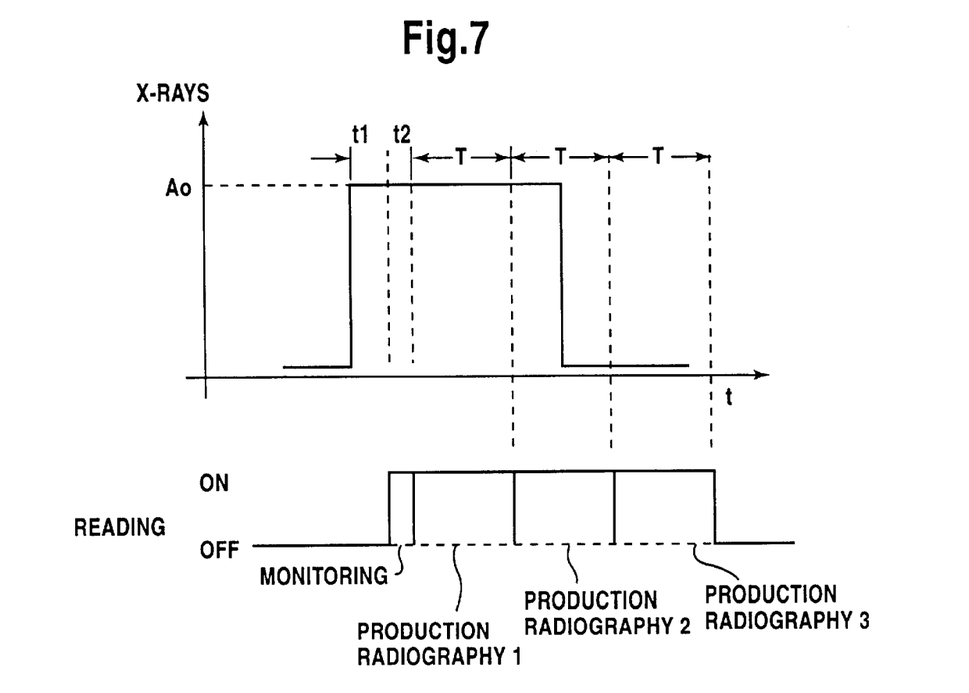
FIG. 7 is a view showing modification 4 of the radiographic sequence.

That is, in modification 4 shown in FIG. 7, signals without charge saturation are collected by production radiographic reading (production radiography 1 to 3) carried out during X-ray irradiation, in the cycles of X-ray irradiating period (T) determined by the equation (2). In the example of FIG. 7, the production radiography is performed three times in total since accumulated charges are read sequentially, column by column, while X rays are emitted. Images acquired through the production radiography performed three times are added to obtain an image similar to where an X-ray sensor with a large dynamic range is used.

Figure 8:
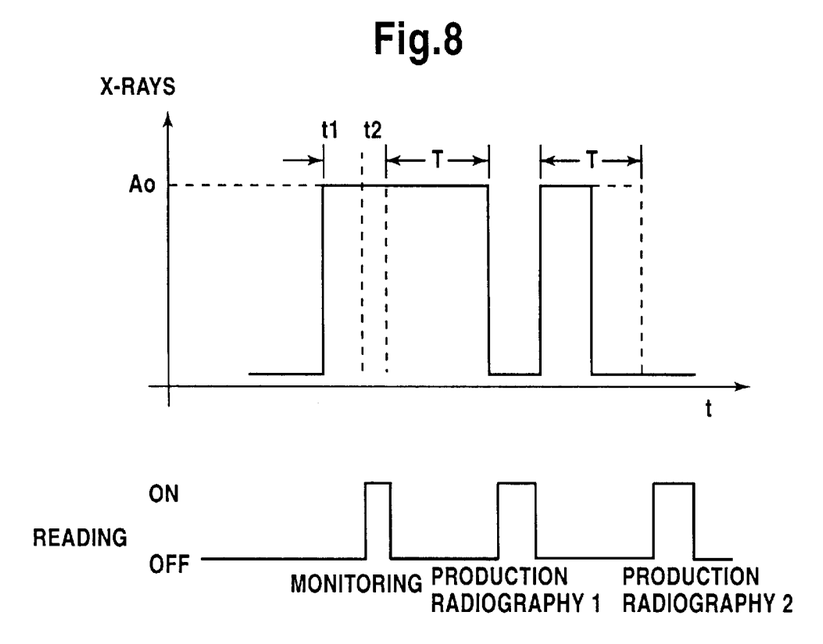
FIG. 8 is a view showing modification 5 of the radiographic sequence.

In modification 5 shown in FIG. 8, a plurality of reading cycles are divided timewise for charge accumulation and reading. The production radiography is performed twice in total since the panel is not irradiated with X rays during reading periods. Images acquired through the production radiography performed twice are added to obtain an image similar to where an X-ray sensor with a large dynamic range is used.

As a variation of modification 5, though not shown in the drawings, X rays may be emitted continuously, and a reset operation as described with reference to FIG. 5 may be carried out immediately after each production radiographic reading.

According to modifications 4 and 5 described above, this invention for performing radiography by a sequence combing monitoring radiography and production radiography achieves a signal collection without charge saturation, with a minimum number of reading times, regardless of the thickness and shape of the examinee.

In the foregoing embodiments, an X-ray irradiating time or X-ray tube current is computed as a radiographic condition for production radiography. This invention is not limited thereto. Various other radiographic conditions (e.g. an X-ray tube voltage) may be determined to optimize a desired quantity of signals for production radiography.

In the foregoing embodiments, this invention is applied to a radiographic apparatus of what is known as the indirect conversion type having a scintillator acting as an X-ray converting layer, with fluorescence thereof converted by photodiodes into signal charges to be accumulated in the pixels. This invention is not limited thereto, but may be applied to a radiographic apparatus of what is known as the direct conversion type having a photoconductive (or X-ray conductive) layer of a-Se or CdTe acting as an X-ray converting layer to accumulate signal charges in the pixels.

Further, this invention is applicable also to a radiographic apparatus for acquiring gamma-ray penetration images instead of X-ray penetration images.

The present invention may be embodied in other specific forms without departing from the spirit or essential attributes thereof and, accordingly, reference should be made to the appended claims, rather than to the foregoing specification, as indicating the scope of the invention.

What is claimed is:

1. A radiographic apparatus using a two-dimensional radiation sensor, comprising:
   a radiation generator for irradiating an examinee;
   said two-dimensional radiation sensor having detecting elements in a two-dimensional array for converting radiation transmitted through said examinee into charge signals, and switches connected to said detecting elements, respectively;
   a gate driving circuit for successively driving, column by column, said switches connected to said detecting elements of said two-dimensional radiation sensor;
   a signal reading circuit for transducing to voltages, amplifying and digitizing electric charges outputted from data lines of said two-dimensional radiation sensor;
   a control circuit for controlling said gate driving circuit and said signal reading circuit;
   a sequence controller for controlling a radiation generating sequence of said radiation generator to perform a monitoring radiography and a subsequent, production radiography with respective radiographic conditions; and
   a radiographic condition computing unit for computing a radiographic condition for said production radiography based on a ratio between a quantity of charges collected from said two-dimensional radiation sensor through said signal reading circuit in time of said monitoring radiography and a desired quantity of charges in time of said production radiography, and on system set values for said monitoring radiography and said production radiography, and applying said radiographic condition for said production radiography at least to said sequence controller.

2. An apparatus as defined in claim 1, wherein said radiographic condition computing unit is operable to compute an irradiating period as said radiographic condition for said production radiography, based on tube current values of said radiation generator set for said monitoring radiography and said production radiography, respectively.

3. An apparatus as defined in claim 2, wherein said radiographic condition computing unit is operable to regard, as said quantity of charges collected, an integrated value of charges of those of said detecting elements present in a region of interest among the charges of said detecting elements of said two-dimensional radiation sensor acquired through said monitoring radiography, and to compute said irradiating period based on a ratio between said quantity of charges collected and an integrated value of a desired quantity of charges in said region of interest in time of said production radiography, and on said tube current values of said radiation generator set for said monitoring radiography and said production radiography, respectively.

4. An apparatus as defined in claim 2, wherein said radiographic condition computing unit is operable to regard, said quantity of charges collected, a charge of one of said detecting elements having a maximum value in a region of interest among the charges of said detecting elements of said two-dimensional radiation sensor acquired through said monitoring radiography, to regard, as said desired quantity of charges, a maximum charge within a range where said two-dimensional radiation sensor has linear input/output characteristics, and to compute said irradiating period based on a ratio between said quantity of charges collected and said desired quantity of charges, and on said tube current values of said radiation generator set for said monitoring radiography and said production radiography, respectively.

5. An apparatus as defined in claim 1, wherein said radiographic condition computing unit is operable to compute a tube current of said radiation generator as said radiographic condition for said production radiography based on radiating periods set for said monitoring radiography and said production, respectively.

6. An apparatus as defined in claim 5, wherein said radiographic condition computing unit is operable to regard, as said quantity of charges collected, an integrated value of charges of those of said detecting elements present in a region of interest among the charges of said detecting elements of said two-dimensional radiation sensor acquired through said monitoring radiography, and to compute said tube current of said radiation generator based on a ratio between said quantity of charges collected and an integrated value of a desired quantity of charges in said region of interest in time of said production of radiograph, and on said radiating periods set for said monitoring radiography and said production radiography, respectively.

7. An apparatus as defined in claim 5, wherein said radiographic condition computing unit is operable to regard, as said quantity of charges collected, a charge of one of said detecting elements having a maximum value in a region of interest among the charges of said detecting elements of said two-dimensional radiation sensor acquired through said monitoring radiography, to regard, as said desired quantity of charges, a maximum charge within a range where said two-dimensional radiation sensor has linear input/output characteristics, and to compute said tube current of said radiation generator based on a ratio between said quantity of charges collected and said desired quantity of charges, and on said radiating periods set for said monitoring radiography and said production radiography, respectively.

8. An apparatus as defined in claim 1, wherein said sequence controller is operable, when said desired quantity of charges exceeds a maximum quantity within a range where said two-dimensional radiation sensor has linear input/output characteristics, to control said radiation generating sequence to carry out said production radiography a plurality of times, whereby the charges of said detecting elements of said two-dimensional radiation sensor acquired through said production radiography carried out once fall within said range where said two-dimensional radiation sensor has linear input/output characteristics.

9. An apparatus as defined in claim 1, wherein said control circuit is operable to cause said gate driving circuit to apply a reset signal to said two-dimensional radiation sensor after charges are read from said detecting elements of said two-dimensional radiation sensor and before commencement of said production radiography.

10. An apparatus as defined in claim 1, wherein said sequence controller is operable to control said radiation generating sequence to emit X rays for said monitoring radiography, then to stop emitting X rays, and thereafter to emit X rays for said production radiography, and said control circuit is operable to control said gate driving circuit and said signal reading circuit to read the charges from said two-dimensional radiation sensor during an X-ray non-emission period following said monitoring radiography and preceding said production radiography.

11. An apparatus as defined in claim 1, wherein said sequence controller is operable to control said radiation generating sequence to emit X rays continuously for said monitoring radiography and said production radiography, and said control circuit is operable to control said gate driving circuit and said signal reading circuit to read the charges from said two-dimensional radiation sensor while X rays are emitted for said monitoring radiography.

12. An apparatus as defined in claim 11, wherein said radiographic condition computing unit is operable to adjust the charges read from said two-dimensional radiation sensor according to variations in a period for irradiating X rays for said monitoring radiography.

* * * * *